US00PP16689P2

(12) United States Plant Patent
Vlielander

(10) Patent No.: US PP16,689 P2
(45) Date of Patent: Jun. 20, 2006

(54) ***KALANCHOE* PLANT NAMED 'PARINA'**

(50) Latin Name: *Kalanchoe blossfeldiana*
Varietal Denomination: Parina

(75) Inventor: Ike Vlielander, De Lier (NL)

(73) Assignee: Fides Goldstock Breeding B.V., De Lier (NL)

( * ) Notice: Subject to any disclaimer, the term of this patent is extended or adjusted under 35 U.S.C. 154(b) by 65 days.

(21) Appl. No.: 11/021,991

(22) Filed: Dec. 24, 2004

(51) Int. Cl.
*A01H 5/00* (2006.01)

(52) U.S. Cl. ..... Plt./337

(58) Field of Classification Search ..... Plt./335, Plt./337, 339, 341
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Kalanchoe* plant named 'Parina', characterized by its numerous large red purple-colored flowers; upright, uniform and compact plant habit; freely branching growth habit; dark green glossy leaves; early flowering; and excellent postproduction longevity.

1 Drawing Sheet

Botanical designation: *Kalanchoe blossfeldiana.*
Cultivar denomination: 'Parina'.

BACKGROUND OF THE INVENTION

The present invention relates to a new and distinct cultivar of *Kalanchoe* plant, botanically known as *Kalanchoe blossfeldiana*, and hereinafter referred to by the name 'Parina'.

The new *Kalanchoe* is a product of a planned breeding program conducted by the Inventor in De Lier, The Netherlands. The objective of the breeding program was to create new freely-branching and freely-flowering *Kalanchoe* cultivars with attractive foliage and flower coloration.

The new *Kalanchoe* originated from a cross made by the Inventor in 1999 of the *Kalanchoe blossfeldiana* cultivar Guntur, not patented, as the female, or seed, parent with the *Kalanchoe blossfeldiana* cultivar Lican, disclosed in U.S. Plant Pat. No. 12,152, as the male, or pollen, parent. The cultivar Parina was discovered and selected by the Inventor as a flowering plant within the progeny of the stated cross in a controlled environment in De Lier, The Netherlands.

Asexual reproduction of the new *Kalanchoe* by terminal vegetative cuttings at De Lier, The Netherlands, since 1998 has shown that the unique features of this new *Kalanchoe* are stable and reproduced true to type in successive generations.

BRIEF SUMMARY OF THE INVENTION

The cultivar Parina has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Parina'. These characteristics in combination distinguish 'Parina' as a new and distinct cultivar:

1. Large and numerous red purple-colored flowers.
2. Upright, uniform and compact plant habit.
3. Freely branching growth habit.

4. Dark green-colored glossy leaves.
5. Early flowering.
6. Excellent postproduction longevity.

Plants of the new *Kalanchoe* can be compared to plants of the female parent, the cultivar Guntur. In side-by-side comparisons conducted by the Inventor in De Lier, The Netherlands, plants of the new *Kalanchoe* differed from plants of the cultivar Guntur in the following characteristics:

1. Plants of the new *Kalanchoe* were more compact than plants of the cultivar Guntur.
2. Plants of the new *Kalanchoe* had smaller leaves than plants of the cultivar Guntur.
3. Flower color of plants of the new *Kalanchoe* was darker than flower color of plants of the cultivar Guntur.

Plants of the new *Kalanchoe* can be compared to plants of the male parent, the cultivar Lican. In side-by-side comparisons conducted by the Inventor in De Lier, The Netherlands, plants of the new *Kalanchoe* differed from plants of the cultivar Lican in the following characteristics:

1. Plants of the new *Kalanchoe* were more compact than plants of the cultivar Lican.
2. Plants of the new *Kalanchoe* had smaller leaves than plants of the cultivar Lican.
3. Plants of the new *Kalanchoe* flowered earlier than plants of the cultivar Lican.
4. Plants of the new *Kalanchoe* and the cultivar Lican differed in flower color.

Plants of the new *Kalanchoe* can also be compared to plants of the *Kalanchoe* cultivar Segula, disclosed in U.S. Plant Pat. No. 13,580. In side-by-side comparisons conducted by the Inventor in De Lier, The Netherlands, plants of the new *Kalanchoe* differed from plants of the cultivar Segula in the following characteristics:

1. Plants of the new *Kalanchoe* were more compact than plants of the cultivar Segula.
2. Flower color of plants of the new *Kalanchoe* was darker red purple than flower color of plants of the cultivar Segula.

BRIEF DESCRIPTION OF THE PHOTOGRAPH

The accompanying colored photograph illustrates the overall appearance of the new *Kalanchoe*, showing the colors as true as it is reasonably possible to obtain in colored reproductions of this type. Colors in the photograph may differ slightly from the color values cited in the detailed botanical description which accurately describe the colors of the new *Kalanchoe*. The photograph comprises a side perspective view of a typical potted plant of 'Parina'.

DETAILED BOTANICAL DESCRIPTION

In the following description, color references are made to The Royal Horticultural Society Colour Chart except where general terms of ordinary dictionary significance are used. Plants used for the aforementioned photograph and for the description were grown during the autumn in De Lier, The Netherlands, in a glass-covered greenhouse. During the production of the plants, day temperatures ranged from 20 to 25° C.; night temperatures ranged from 19 to 21° C.; and light levels ranged from 10,000 to 50,000 lux. Unrooted cuttings were directly stuck in 12.5-cm containers and received long day/short night conditions (more than 14 hours of light) for about three weeks; plants then received photoinductive short day/long night conditions (minimum 14 hours darkness) until flowering. Plants were about 13 weeks old from an unrooted cutting when the photograph and the description were taken.

Botanical classification: *Kalanchoe blossfeldiana* cultivar Parina.

Parentage:

*Female or seed parent.*—*Kalanchoe blossfeldiana* cultivar Guntur, not patented.

*Male, or pollen, parent.*—*Kalanchoe blossfeldiana* cultivar Lican, disclosed in U.S. Plant Pat. No. 12,152.

Propagation:

*Type cutting.*—Terminal vegetative cuttings.

*Time to initiate roots.*—Summer: About 12 days at 21° C. Winter: About 15 days at 21° C.

*Time to produce a rooted cutting.*—Summer: About 21 days at 21° C. Winter: About 28 days at 21° C.

*Root description.*—Numerous, fine, fibrous, and well-branched.

Plant description:

*Form.*—Upright, uniform and compact plant habit. Very freely flowering with numerous compound cymes. Inverted triangle with rounded crown. Appropriate for 10 to 15-cm containers.

*Crop time.*—About 11 to 14 weeks: 3 to 4 weeks under long day/short night conditions followed by 8 to 10 weeks of short day/long night conditions. Moderately vigorous growth rate.

*Plant height at flowering.*—About 17 cm.

*Plant diameter at flowering.*—About 15 cm.

*Branching habit.*—Freely branching; typically seven to eight lateral branches develop per plant. Pinching (removal of terminal apex) is not required but will enhance lateral branch development.

*Lateral branch description.*—Length: About 11 to 15 cm. Diameter: About 3 to 6 mm. Internode length: About 1.5 to 2.5 cm. Aspect: Erect. Strength: Moderately strong. Texture: Smooth, glabrous. Color: 147A.

*Foliage description.*—Leaves simple, opposite, generally symmetrical. Quantity per plant: About 7 to 11 mature leaves and 10 to 17 generative leaves. Length: About 8 cm. Width: About 5 cm. Shape: Ovate to elliptic. Apex: Acute. Base: Acute. Margin: Crenate. Texture: Leathery, glabrous and succulent. Color: Developing and fully expanded leaves, upper surface: 147A; glossy. Developing and fully expanded leaves, lower surface: 147B. Venation, upper surface: 147A. Venation, lower surface: 147B. Petiole length: About 1.2 cm. Petiole diameter: About 3 mm by 7 mm. Petiole color, upper and lower surfaces: 147A to 147B.

Flower description:

*Flower type and habit.*—Single flowers arranged in compound dichasial cymes that arise from leaf axils. Freely flowering; more than 25 open flowers per lateral branch and more than 150 open flowers per plant. Flowering continuously for at least seven weeks. Flowers persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about eight to ten weeks are required. Actual time to flower is primarily dependent upon temperature and light intensity.

*Post-production longevity.*—Excellent post-production longevity; plants maintain good foliage and flower substance for about 59 days under interior environmental conditions. Individual flowers last about 24 days on the plant.

*Flower diameter.*—About 1.7 cm.

*Flower height.*—About 1.4 cm.

*Flower buds.*—Shape: Initially oblong, becoming tubular ovoid with development. Length: About 1 cm. Width: About 4 mm. Color: Initially, 138C, then 63D with development.

*Petals.*—Quantity: Four fused at base. Length: About 7 mm. Width: About 6 mm. Aspect: Flat to slightly upright. Shape: Ovate. Apex: Obtuse. Margin: Entire. Texture: Glabrous, smooth. Color: When opening and fully opened, upper surface: 66B; color becoming closer to 66B to 66C. When opening and fully opened, lower surface: 70D.

*Sepals.*—Quantity: Four fused at base. Length: About 5 mm. Width: About 1.5 mm. Aspect: Erect. Shape: Oblong. Apex: Acute. Base: Obtuse. Margin: Entire. Texture: Glabrous, smooth. Color, upper and lower surfaces: 137D.

*Peduncles.*—Length: About 3 to 8 mm. Diameter: About 2 mm. Aspect: Erect. Strength: Strong, flexible. Texture: Smooth, leathery. Color: 138C.

*Reproductive organs.*—Stamens: Quantity per flower: Eight. Anther shape: Elliptic; flat. Anther size: About 0.3 mm. Anther color: Close to 150D. Pollen amount: Scarce. Pollen color: Close to 12A. Pistils: Quantity per flower: Four. Style length: About 1 mm. Style color: 138D. Stigma shape: Flat, rounded. Stigma color: 8D. Ovary color: 138D.

*Seed.*—Length: About 0.1 mm. Diameter: About 0.05 mm. Color: Close to 166C.

Disease/pest resistance: Plants of the new *Kalanchoe* have not been observed to be resistant to pathogens and pests common to *Kalanchoes*.

Temperature tolerance: Plants of the new *Kalanchoe* have been observed to tolerate low temperatures of 16° C. and high temperatures of 35° C.

Garden performance: Plants of the new *Kalanchoe* perform have been observed to perform well in the garden and are tolerant to rain and wind.

It is claimed:

1. A new and distinct cultivar of *Kalanchoe* plant named 'Parina', as illustrated and described.

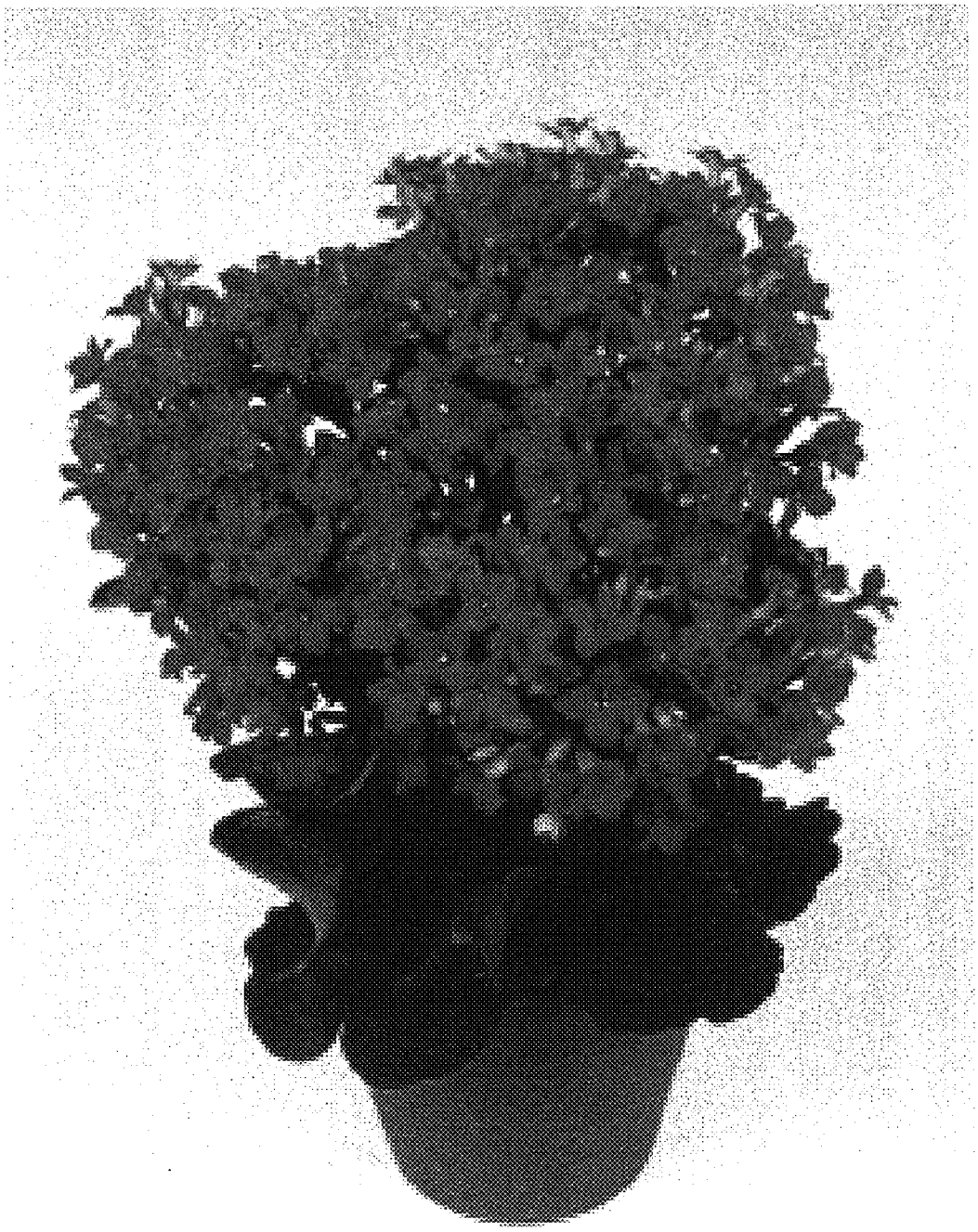

* * * * *